United States Patent [19]

Sarkozi

[11] Patent Number: 5,029,577

[45] Date of Patent: * Jul. 9, 1991

[54] SELF ADJUSTING, SOFT NECK SUPPORT COLLAR

[76] Inventor: Jeff Sarkozi, 1117 N. Avila Pl., Orange, Calif. 92669

[*] Notice: The portion of the term of this patent subsequent to Sep. 25, 2007 has been disclaimed.

[21] Appl. No.: 571,713

[22] Filed: Aug. 24, 1990

Related U.S. Application Data

[63] Continuation-in-part of Ser. No. 415,872, Oct. 2, 1989, Pat. No. 4,958,631.

[51] Int. Cl.⁵ .............................................. A61F 5/00
[52] U.S. Cl. ................................................. 128/87 B
[58] Field of Search .............. 128/DIG. 23, 87 B, 75; 2/415

[56] References Cited

U.S. PATENT DOCUMENTS 4,958,631  9/1990  Sarkozi .............................. 128/87 B Primary Examiner—Richard J. Apley
Assistant Examiner—Glenn E. Richman
Attorney, Agent, or Firm—Willie Krawitz

[57] ABSTRACT

A soft neck support collar is disclosed comprising two offset and attached, tubular ring elements, each element hooking together at their respective ends. Both ring elements contain a soft fill material such as nylon, cotton, polyester, acrylics, foam, foam chips, etc. The combined effect of the fill material together with the tubular configuration, enables the neck to adjust for lateral forward and backward forces during movement. The upper ring element is tapered at each end, so that when these ends are joined together, a space is formed into which the chin can fit, thereby maintaining the neck in a neutral position, and preventing hyperextension.

The lower ring element is hooked together at each end, and the rings are offset to enable the lower ring to close at the back of the neck, approximately opposite from the closure of the upper ring element. Hence, the lower ring element functions as a continuous, uniform tubular-shaped ring which does not interfere with movement of the chin. Thus, in the closed configuration, the neck support collar allows for neutral positioning of the chin and neck, and restricts neck mobility.

9 Claims, 2 Drawing Sheets

SELF ADJUSTING, SOFT NECK SUPPORT COLLAR

This application is a continuation-in-part of U.S. Ser. No. 415,872, filed Oct. 2, 1989, and issued on Sept. 25, 1990 as U.S. Pat. No. 4,958,631.

BACKGROUND OF THE INVENTION

This invention relates to a new and improved self adjustable, soft neck support collar which adjusts for and restrains lateral, forward and backward movement of the neck to ensure neutral positioning of the chin and neck.

A wide variety of neck support collars are in the market, and typical collars are disclosed in U.S. Pat. Nos. 1,964,962; 2,389,690; 2,806,471; 3,964,474; 4,582,051; 4,700,697; and, 4,708,129. Some of these patents describe devices which are air inflatable, and while these devices provide support for a user's neck, this support obviously will not be adjustable, since air is the supporting medium. Other of these patented devices are fairly complicated collars which are expensive, and still other such devices require adjustable straps. Other patents show soft, unitary, solid foam neck support collars, but they fail to provide sufficient resiliency when the neck is at rest, and do not provide enough resistance to lateral, forward or backward bending of the neck. Also, solid foam block materials in general tend to buckle about midway along their length due to applied pressure caused by neck motion.

It would be desirable to provide a soft neck support device which has a simple construction and is inexpensive to manufacture. Also, the device should impart suitable neck restraint, and is self adjusting in the sense that as the user's neck moves from away from an erect position, the neck support provides increasing resistance in the direction of neck motion, rather than buckling.

THE INVENTION

According to the invention, there is provided an adjustable neck support comprising two attached, superposed tubular elements connected at their respective ends, each element containing a soft fill material, and both elements being sized and shaped to fit around a user's neck.

The upper tubular element is tapered at each end, so that upon closure it defines an open shape which fits into the user's chin. The lower tubular element is offset to the upper element, so that when the ends of the lower tubular element are connected, they will close at the rear of the neck, without interfering with the operation of the upper tubular element. Generally, the lower tubular element is closed at the back of the user's neck.

The soft fill material employed in the tubular elements is typically cotton, polyester, nylon, acrylic polymers, foam, chip foam, etc. These materials provide a neck support which permits the user's neck to be comfortably supported, and which will readily adjust to the weight and configuration of the chin and neck, when at rest. When the neck and chin deviate from an erect position, they will cause the neck support to become deformed, without buckling, and also provide a progressively increasing support as the neck and chin increasingly deviate from the erect position, until little or no further movement occurs.

DESCRIPTION OF THE PREFERRED EMBODIMENTS

Figure 1:
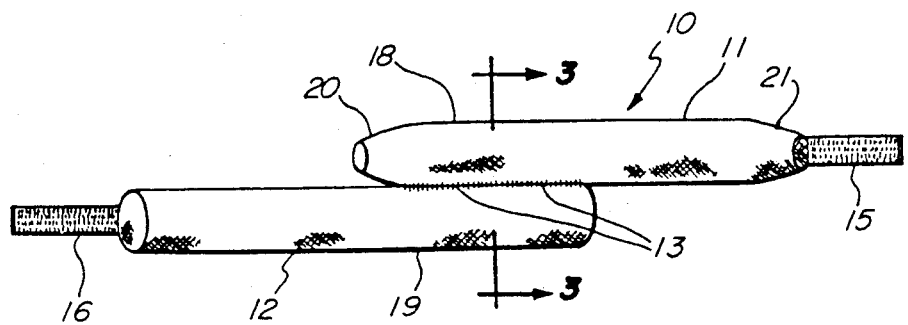
FIG. 1 is an external view in side elevation, showing the adjustable neck support of this invention.
Figure 2:
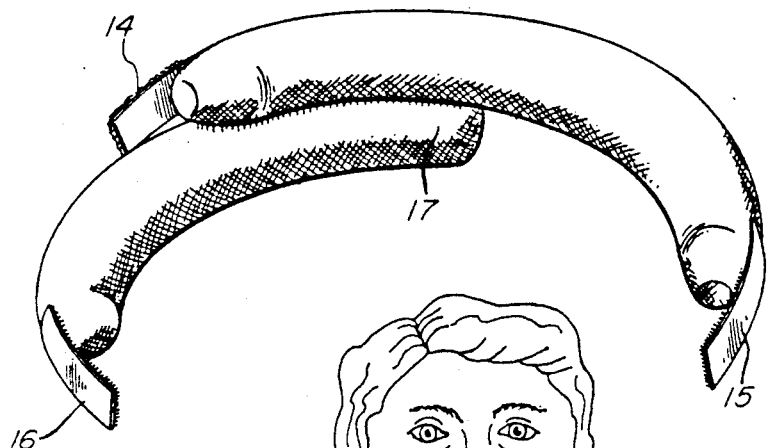
FIG. 2 is a perspective view of the neck support.

The adjustable neck support 10 of this invention is shown in FIGS. 1 and 2, and comprises upper and lower tubular elements 11 and 12, offset with respect to each other, and joined by a plurality of stitchings 13 entirely along the overlapping areas of the tubular elements; this secures the tubular elements together against relative motion. In use, the respective ends of the tubular elements 11 and 12 are joined together by fasteners 14, 15 and 16, 17 which may be constructed of VELCRO, hook elements, laces, etc.

Figure 3:
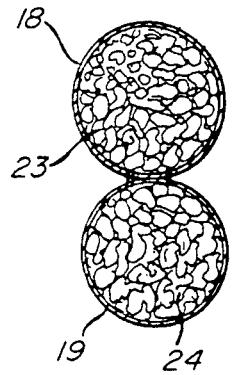
FIG. 3 is a cross sectional view of the neck support, taken along lines 3—3 of FIG. 1.

The covering materials 18, 19 of the respective tubular elements 11 and 12 are preferably constructed of woven cloth such as cotton, polyester, nylon, acrylic polymers, and blends of these, etc. As shown in FIG. 3, the interiors 23, 24 of the tubular elements contain a soft fill, such as cotton, polyester, nylon, acrylic polymers, fiber fill, loose gauze, down, foam, chip foam, etc., and mixtures of these.

Figure 4:
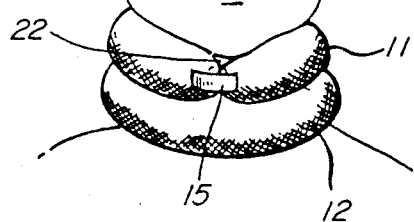
FIG. 4 is a front elevation view showing the neck support installed around a user's neck.

As shown in FIGS. 1 and 2, each end of the upper tubular element 11 is tapered 20, 21 so that upon closure, a chin support 22 is formed where the ends meet. Thus, when the neck support 10 is installed, as shown in FIG. 4, the chin of the user fits into, and is supported in an appropriate position by the chin support. Also, when the lower tubular element 12 is closed at the back of the user's neck, it will then form a continuous ring. Hence, the user's chin is supported and fixed in position by the chin support, and the chin support in turn is supported by the lower tubular element. The soft fill of the interiors 23, 24 of the tubular elements in this configuration is sufficiently flexible to self adjust for different shapes, sizes and weights of the user's neck and chin regions.

Figures 5, 6:
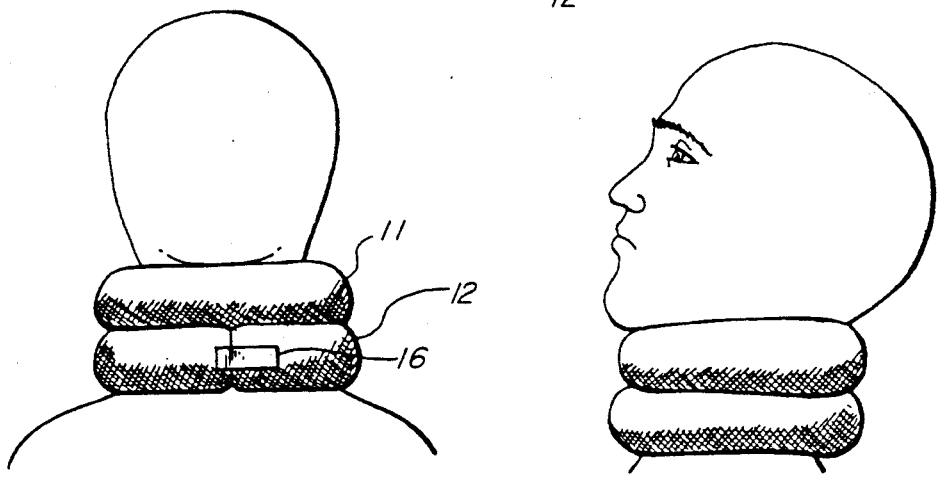
FIG. 5 is a rear elevation view of the installed neck support.
FIG. 6 is a side elevation view of the installed neck support.

FIGS. 4, 5 and 6 illustrate the device when installed, and as shown in these three figures, the neck support 10 will maintain the neck aligned in the erect position.

As indicated, one of the unique features of this invention is the capability of maintaining a resilient support which increases as the user's neck and chin deviate from the erect position.

Additionally, another unique feature of this invention enables the extent of resilience to be varied by employing a particular fill material, or by varying the size and packing density of the fill, or by adjusting the diameter of the tubular elements, or by any combination thereof.

The tubular elements 11 and 12 vary in size from about 1"–4" in diameter, and have different lengths, depending on user neck sizes. Furthermore, their simple design makes them easy and inexpensive to manufacture. Also, the orientation of the tubular components with respect to each other permits them to self adjust to the user at rest, as well as during movement of the neck and chin without undue discomfort, considering the typical nature of the user's medical problem. invention shown in FIGS. 1-6 are considered to represent the more usual mode of carrying out this invention, specific situations may arise where it would be preferred to enable the patient to have greater flexibility during treatment, particularly in the latter stages of recovery.

Figure 7:
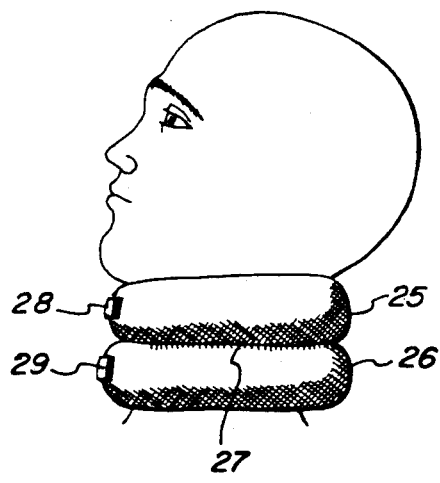
FIG. 7 is an external view in side elevation, showing a modification of the neck support installed around a user's neck.
Figure 9:
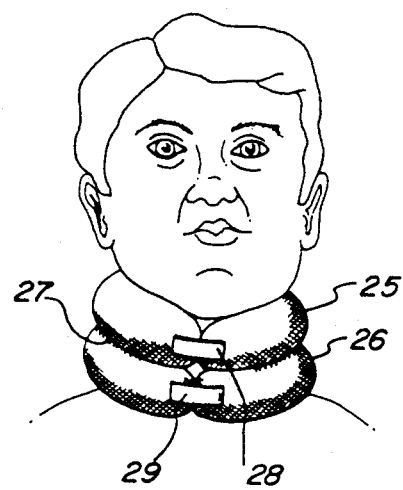
FIG. 9 is a front elevation view showing the neck support of FIG. 7.

To achieve this purpose, as shown in FIGS. 7 and 9, upper and lower tubular elements 25 and 26 are oriented with respect to each other so that they coincide with respect to each other, rather than being offset. In this latter embodiment, the tubular elements 25, 26 are joined along their entire lengths by a plurality of stitchings 27, thereby securing them against relative motion. This of course will provide a better reinforced device compared to the offset mode of the tubular elements shown in FIGS. 1-6. As shown in FIGS. 7 and 9, the respective ends of the tubular elements 25 and 26 are joined together by fasteners 28 and 29 so that when installed, they coincide under the patient's chin. This may provide greater flexibility in movement of the patient's chin. Also, this provides the most convenient method for closing the tubular elements for individuals with limitations of shoulder, arm or hand functions.

Figure 8:
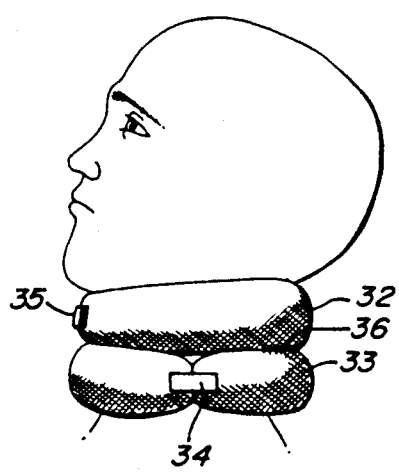
FIG. 8 is an external view in side elevation, showing another modification of the neck support installed around a user's neck.
Figure 10:
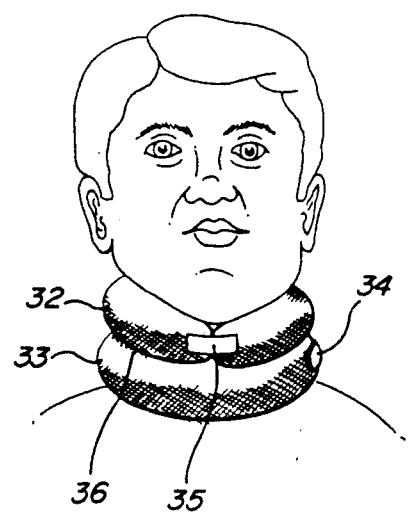
FIG. 10 is a front elevation view showing the neck support of FIG. 8.

In the embodiment shown in FIGS. 8 and 10, the offset mode of tubular elements 32 and 33 are joined by stitchings 36, and the upper tubular element 32 is closed by fastener 35. The lower tubular element 33 is closed by a fastener 34 at one side of the patient's neck rather than at the back, as shown in FIG. 5. The embodiment shown in FIGS. 8 and 10 would be particularly useful if muscle stiffness or discomfort in an area of the neck limits the ability of users to raise their arms and manipulate the lower tubular element.

I claim:

1. A self adjusting, soft, neck support collar, comprising:
   a. an upper, tubular-shaped element providing an outer, woven cloth covering material and an interior which contains a soft fill material, the tubular-shaped element defining tapered ends which are adapted for closure under a user's chin by closure elements mounted at each end, to thereby form a ring which fits upwardly around a user's neck; and,
   b. a lower, tubular-shaped element providing an outer, woven cloth covering material, and shaped to form an interior which contains a soft fill material, the lower tubular-shaped element being adapted for closure at each end by closure elements to form a ring which fits around the lower portion of the user's neck, the upper tubular element resting on and being joined to the lower tubular element; whereby,
      i. the tapered closure portion of the upper element and adjacent lower, tubular element define a chin support for the user; and,
      ii. the soft fill materials in the interiors of the upper and lower tubular elements function to: 1. impart a flexible support for the user's neck and chin which self adjust for different shapes, sizes and weights of the user's neck and chin regions; 2. maintain a resilient support which increases as the user's neck and chin deviate from an erect position during motion; and, 3. self adjust to the user in a rest position.

2. The neck support collar of claim 1, in which the outer woven covering of the tubular neck support elements is selected from the class consisting of cotton, nylon, polyester, acrylics, and blends thereof.

3. The neck support collar of claim 2, in which the soft fill interiors of the tubular neck support elements are selected from the class consisting of cotton, nylon, polyester, acrylic polymers, fiber fill, loose gauze, foam, chip foam, down, and mixtures thereof.

4. The neck support collar of claim 1, in which the lower tubular ring functions as a continuous, uniform, tubular-shaped ring upon closure.

5. The neck support collar of claim 4, in which the lower tubular ring closes at the back of the user's neck approximately opposite from the closure of the upper, tubular ring.

6. The neck support of claim 1, in which the upper, and lower tubular rings are joined together by sewing.

7. The neck support of claim 1, in which the resilience of the rings depends on the soft fill material being employed, by the size and packing density of the material, and by ring diameter.

8. The neck support of claim 1, in which the tubular elements are stacked in coincidence along their lengths, and both elements upon closure fit under the user's neck.

9. The neck support of claim 1, in which the closure portion of the lower tubular element is positioned at the side of the user's neck.

* * * * *